US005498823A

United States Patent [19]

Noble et al.

[11] Patent Number: 5,498,823

[45] Date of Patent: Mar. 12, 1996

[54] ION-EXCHANGE SUPPORTS FOR FACILITATED TRANSPORT MEMBRANES WITH ENHANCED SELECTIVITY

[75] Inventors: Richard D. Noble; Paul M. Thoen, both of Boulder; Carl A. Koval, Golden, all of Colo.

[73] Assignee: Regents of the University of Colorado, Boulder, Colo.

[21] Appl. No.: 189,563

[22] Filed: Feb. 1, 1994

[51] Int. Cl.[6] .............................. C07C 7/144; C07C 7/10

[52] U.S. Cl. .......................... 585/818; 585/819; 210/644; 210/649; 210/650; 210/651

[58] Field of Search .................................... 585/818, 819; 210/644, 649, 650, 651

[56] References Cited

U.S. PATENT DOCUMENTS

| | | | |
|---|---|---|---|
| 3,758,605 | 9/1973 | Hughes et al. | 260/677 A |
| 4,614,524 | 9/1986 | Kraus | 55/16 |
| 5,191,151 | 3/1993 | Eriksen et al. | 585/818 |

OTHER PUBLICATIONS

Funke, Hans H. et al, "Separation of Gaseous Olefin Isomers Using Facilitated Transport Membranes", pp. 229–236, (1993) Journal of Membrane Science, 82.

Thoen, P. M., et al, "Unexpectedly Large Selectivities for Olefin Separations Utilizing Silver Ion in Ion–Exchange Membranes", pp. 1262–1269, (1994), The Journal of Physical Chemistry.

*Primary Examiner*—Sharon Gibson
*Attorney, Agent, or Firm*—Fay, Sharpe, Beall, Fagan, Minnich & McKee

[57] ABSTRACT

This invention relates to a method for effectively separating an unsaturated hydrocarbon from a feedstock containing at least two similar unsaturated hydrocarbons comprising passing the feedstock over one side of an ionopore membrane charged with a facilitator having an affinity for each of the at least two similar unsaturated hydrocarbons and recovering from a second side of the membrane permeate containing predominantly one of the at least two similar unsaturated hydrocarbons, the similar unsaturated hydrocarbons being selected from the group consisting essentially of aromatic, alkene, and diene hydrocarbons.

This invention further relates to a method for achieving liquid phase separation of at least two competing components from a feedstock containing the components such that the separation factor for the competing components is at least about 4 times the separation factor calculated when permeating single components using the same membrane and under the same conditions.

20 Claims, No Drawings

ION-EXCHANGE SUPPORTS FOR FACILITATED TRANSPORT MEMBRANES WITH ENHANCED SELECTIVITY

BACKGROUND OF THE INVENTION

This invention relates to a process for achieving enhanced selectivities in liquid phase separations using ion-exchange membranes exchanged with suitable olefin facilitators which exhibit unexpectedly large selectivities for the separation of multi-component mixtures of similar unsaturated hydrocarbons. Specifically, this invention relates to perfluorosulfonate ionomer membranes cast from solution and ion-exchanged with silver$^+$ ion and exhibiting enhanced selectivities for the separation of aromatic/aromatic, alkene/aromatic, and alkene/diene mixtures is disclosed.

Due to their extensive use in the polymer industry and as solvents, there is a continuing need for better separating processes for alkenes and other unsaturated olefinic or aromatic organic compounds. Recent studies by the U.S. Department of Energy and others indicate that membrane-based separation processes for a variety of compounds are desirable, provided that membrane performance can be improved. One method for improving membrane performance is via carrier-mediated or facilitated transport. In membrane separation processes using facilitated transport, a carrier provides an additional pathway for a permeate to cross the membrane, thereby increasing the fluxes and separation factors relative to the permeates that are not facilitated by the carrier.

There are several reports of facilitated transport of olefins (single component or olefin/saturate separation) using immobilized $AgNO_3$ solutions (Hughes et al. U.S. Pat. No. 3,758,605; Hughes et al., "Recent Developments In Separation Science", Vol. 173–199 (1986); Teramoto et al., *J. Chem. Eng.*, Japan (19) 5,419–424 (1986). Hughes, Mahoney, and Steigelmann (1986) presented the results of a bench and pilot scale study of ethylene and propylene transport using aqueous $Ag^+$ solutions immobilized in asymmetric, porous hollow fiber reverse osmosis membranes at ambient temperature. The ethylene/ethane separation factor for a 2M $AgNO_3$ immobilized liquid membrane (ILM) was 243 at an ethylene partial pressure of 95 cm Hg. Teramoto et al. (1986) also studied ethylene transport with immobilized $AgNO^+$ aqueous solutions at ambient temperature. They found selectivity for ethylene over ethane of approximately 1000 when the $AgNO_3$ concentration was 4M and the ethylene partial pressure was 37 cmHg.

Solvent swollen ionomer films have been used as supports for ionic complexation agents in order to improve the ability of facilitated transport membranes for gas and liquid phase olefin transport (LeBlanc et al., *J. Mem. Sci.*, Vol. 6, 339–343 (1980) Kraus, U.S. Pat. No. 4,614,524; Koval et al., *I & EC Res.*, 28, 1020–1024, (1989); Koval et al., *J.A.C.S.*, 110, 293–295(1988). Use of ionomer materials has been shown to improve the stability of facilitated transport membranes because the support is non-porous and the carrier cannot be removed from the membrane except by an ion-exchange reaction.

LeBlanc et al. reported ethylene transport using a $Ag^+$ counterion carrier in a water saturated sulfonated poly(dimethylphenylene oxide) cation exchange membrane at ambient temperature. Ethylene and ethane permeance in the above system yielded values corresponding to an ideal separation factor of 288.

Kraus (1986) prepared facilitated transport membranes using Nafion® 415 containing an $Ag^+$ carrier. However, following ion-exchange to introduce $Ag^+$ into the membrane, the membrane was dried and soaked in an organic alcohol such as glycerol or octanol. At ambient temperature and pressure, the ethylene/ethane separation factor was 10.

The foregoing demonstrate that liquid membranes and other ion-exchange membranes containing $Ag^+$ exhibit large (>100) separation factors (flux of A/flux of B, corrected for driving force) for alkenes with respect to the alkanes due to reversible alkene-$Ag^+$ complexation reactions. The transport of the alkene is facilitated by the $Ag^+$, while the transport of the alkane is due to other factors, such as Fickian diffusion.

It has remained, however, for the subject invention to provide a method whereby similar molecules, such as aromatic/aromatic, aromatic/alkene, or alkene/diene mixtures can be separated in the liquid phase while achieving unexpectedly high selectivities. Such a process has proven elusive due to the affinity of suitable olefin facilitators for each component of the feed solution, resulting in a phenomenon commonly referred to as competitive transport. Since the equilibrium constants describing the complexation of facilitators with many alkenes and aromatics in aqueous solution are similar, large separation factorsdue to facilitated transport would not be anticipated.

It is an object of the present invention, therefore, to provide a process whereby similar unsaturated hydrocarbons can be effectively separated in the liquid phase using facilitated ion-exchange membranes.

SUMMARY OF THE INVENTION

This invention relates to a method for effectively separating an unsaturated hydrocarbon from a feedstock containing at least two similar unsaturated hydrocarbons comprising passing the feedstock over one side of an ionopore membrane charged with a facilitator having an affinity for each of the at least two similar unsaturated hydrocarbons and recovering from a second side of the membrane permeate containing predominantly one of the at least two similar unsaturated hydrocarbons, the similar unsaturated hydrocarbons being selected from the group consisting essentially of aromatic, alkene, and diene hydrocarbons.

This invention further relates to a method for achieving liquid phase separation of at least two competing components from a feedstock containing the components such that the separation factor for the competing components is at least about 4 times the separation factor calculated when permeating as single components using the same membrane and under the same conditions.

DETAILED DESCRIPTION OF THE INVENTION

The subject invention relates to the incorporation of a suitable facilitator ion into ion-exchange membranes to dramatically enhance the transmembrane fluxes of at least one component of a multi-component mixture containing olefin and/or aromatic components in the liquid phase. Fluxes are enhanced by factors of $10^2$–$10^3$ over expected fluxes using the method disclosed herein. Large separation factors are achieved for mixtures of similar solutes even though the solutes have comparable complexation affinities for the facilitator ion selected or employed. As used herein, "similar hydrocarbons", "similar , molecules", and "similar solutes" refers to the hydrocarbons, molecules, or solutes having similar equilibrium constants with the complexing agent of choice Also, the terms "facilitator", "facilitator ion", "complexing agent", and "carrier" are used interchangably throughout to refer to ions selected for incorporation into ion-exchange membranes to aid in transport of bound hydrocarbon molecules through the ion-exchange membrane.

Using facilitated ion-exchange membranes for separation of olefin and aromatic multi-component mixtures, unexpectedly large selectivities are observed. These selectivities are much larger than predicted from theory and from measurements involving single component feed solutions. Enhanced complexation of the facilitator in the ion-exchange membrane when separating multi-component mixtures results in competitive absorption.

Applications of facilitated transport membranes (FTMs) can be limited by two effects. First, as the concentrations of reactive solutes in the feed mixture increases, the carrier can become saturated. This results in diminished selectivity and often severely limits the concentration range and type of separation processes in which FTMs will be practical. However, using the subject invention, while a decreasing separation factor with increasing feed concentration is seen, selectivities greater than 10 are maintained for feed mixtures containing as much as 50% of a reactive component. This surprising result indicates that the subject facilitated ion-exchange membranes could be utilized in pervaporation or perstraction processes to achieve similar results.

The second possible limiting factor of FTMs is related to the kinetics of the complexation reaction. Normally, the productivity of a membrane is inversely proportional to the membrane thickness (L); therefore, it is desirable to use the thinnest membrane that can be produced without defects. Unfortunately, when the kinetics of the complexation reaction in FTMs are not fast with respect to the diffusion of free solutes, a diminution of separation factor is observed. Membranes ranging from 2.5 to 40 μm in thickness demonstrate that the subject facilitated ion-exchange membranes show no signs of a kinetic limitation, i.e. productivity, or transmembrane flux, increases as 1/L with no loss of selectivity.

In its broadest sense, the subject invention contemplates the use of an ion-exchange membrane to separate multi-component hydrocarbon mixtures wherein the components are similar unsaturated hydrocarbons as defined hereinabove. The ion-exchange membrane may be in the cation or the anion form, this form being determined by the charge of the facilitator selected for the particular components to be separated. The geometry of the ion-exchange membrane may be any form suitable to a particular process or use, for example, the membrane may be cast as a flat sheet, as a spiral wound membrane or as hollow fiber tubes, among other forms.

It is important to the subject invention that the membrane, in whatever form is selected, be cast from solution, or made by other suitable means, to ensure the formation of what is known as ionopore structure within the membrane. This is important because the ionopore structure includes ionic clusters within the membrane connected by channels. With the aid of a number of instrumental techniques such as small angle X-ray scattering (SAXS), IR spectroscopy, NMRand neutron scattering, it has been demonstrated that ionic clusters exist in Nafion® membranes, i.e. in the presence of water, the ionic groups aggregate in such a manner that phase separation takes place, giving rise to a hydrophilic domain (including ions and most absorbed water) and a hydrophobic region (organic matrix). A three-phase model has been proposed wherein it is considered that an interfacial phase which contains a small amount of water, some sulfonate exchange sites and pendant side chain material, exists between the ionic clusters and organic matrix. Many unusual properties of Nafion® membranes can be attributed to such a three-phase morphology. Xue et al., "Characterization of Nafion® Membranes by Transmission Electron Microscopy", *J Mem Sci*, 45, 261–271 (1989).

The subject separation technique, therefore, offers exceptional results when used to separate multi-component mixtures containing similar unsaturated hydrocarbons. The invention will now be discussed more particularly with reference to the preferred embodiment thereof. It is to be understood by the reader, however, that the full breadth of the invention includes all options and variations falling fairly within the meets and bounds of the appended claims, this preferred embodiment being provided merely to more clearly demonstrate the subject invention.

THE PREFERRED EMBODIMENT

A suitable ion-exchange membrane cast from solution, or an ionopore membrane, is a perfluorosulfonic acid (PFSA) membrane. The Nafion® 111 membrane referred to in the following examples is exemplary of a suitable PFSA membrane. When using an ionopore PFSA membrane to separate olefin and/or aromatic multi-component mixtures, $Ag^+$ is one appropriate complexing agent or facilitator due to its affinity for olefins and aromatics. Of course, other appropriate facilitators may be selected by one skilled in the art depending upon the components to be separated.

The membranes used in the following competitive transport examples were Nafion® 111, available commercially from dupont, which has a dry thickness of 25 μm. The membranes may be prepared to specified thickness by casting from solution.

The ion-exchange procedures used to convert the membrane, whether purchased, solution cast, or otherwise formed, to the $Ag^+$ form and the procedures used to measure transmembrane fluxes have been previously reported. Koval et al., *Ind. Eng. Chem. Res.*, 1992, 31, 1116–1122; Koval et al., *Ind. Eng. Chem. Res.*, 1989, 28, 1020–1024; Spontarelli, T. *Ph.D. Thesis, Univ. Col.*, 1989.

The feed side solutions consisted of the solutes of interest in water-saturated isooctane, while the sweep side solutions consisted only of water-saturated isooctane.

For membrane separations, the separation factor for two components (A and B) in the feed mixture, $S_{AB}$, is defined as the ratio of permeabilities (P) or driving-force-corrected transmembrane fluxes (J):

$$S_{AB}=\frac{P_A}{P_B}=\frac{J_A}{J_B}\times\frac{[B]_{Feed}-[B]_{Sweep}}{[A]_{Feed}-[A]_{Sweep}}.$$

For 25 μm Nafion® 111 membranes, styrene/ethylbenzene separation factors of 18 and 33 were measured for multi-component feed solutions containing 1.0M and 0.1M of each solute, respectively. The literature values for the equilibrium constants for $Ag^+$ complexation in aqueous solution are $18M^{-1}$ for styrene and $2.7M^{-1}$ for ethylbenzene Based upon these values, $S_{AB}{}^{Ideal}$ would be 6.7. Subsequent experiments revealed that if membrane fluxes are determined using a single solute in the feed solution, the calculated separation factor would be only 3.5. The multi-component results indicated that competitive absorption into the membrane was occurring.

EXAMPLE 1

The competitive effect between 1,5-hexadiene ($K_{eq}$=$1850M^{-1}$) and 1-hexene ($K_{eq}$=$860M^{-1}$) is summarized in Table I, which reveals that an extremely small amount of 1,5-hexadiene in the feed solution drastically suppresses the flux of 1-hexene. The presence of only 0.01M 1,5-hexadiene in feed solutions containing 0.5M 1-hexene produces a 4-fold reduction in the flux of 1-hexene. Other experiments reveal that the amount of 1-hexene in the feed solution has little or no effect on the flux of 1,5-hexadiene or its concentration in the membrane. Although $S_{AB}^{Ideal}$ is 2.1 for this separation and single-component experiments indicate that $S_{AB}^{Calc}$ is 4.3, an equimolar, multi-component experiment results in a separation factor of 43.

TABLE 1

THE FLUXES OF 1,5-HEXADIENE AND 1-HEXENE THROUGH $Ag^+$ NAFION ® 111

| Feed Concentration (M) | | Flux (mol/cm² · sec × $10^{-9}$) | | Separation |
|---|---|---|---|---|
| 1,5-Hexediene | 1-Hexene | 1,5-Hexadiene | 1-Hexene | Factor |
| 0.00 | 0.50 | — | 4.0 | } 4.3 |
| 0.50 | 0.00 | 17 | — | |
| 0.01 | 0.50 | 1.4 | 1.0 | 70 |
| 0.10 | 0.50 | 5.8 | 0.49 | 59 |
| 0.50 | 0.50 | 19 | 0.44 | 43 |
| 2.0 | 0.50 | 22 | 0.20 | 28 |
| 5.0 | 0.50 | 24 | 0.10 | 24 |

COMPARATIVE EXAMPLE 2

The magnitude of the competitive effect described here for Nafion® 111 appears to be highly dependent on the chemical composition and possibly the internal structure of the ionomer membrane. Under the conditions described above where the 1,5-hexadiene/ 1-hexene separation factor is 43 for a 25 μm Nafion® 111 membrane, the separation factor is 7.8 for an 80 μm cross-linked polyethylene membrane containing carboxylate ion-exchange groups (Raipore PK3060) and is only 2.5 for a 35 μm radiation grafted perfluorosulfonate membrane (Raipore R 1010) that contains a different side chain than Nafion®, neither of which membranes exhibit ionopore structure.

EXAMPLE 3

Experiments were performed using Nafion® 111 ionopore membranes with two aromatic solutes that have small and virtually identical equilibrium constants with $Ag^+$; benzene ($K_{eq}$=2.4$M^{-1}$) and cumene ($K_{eq}$=2.8$M^{-1}$). In this case, the ideal separation factor is only 0.86 and transmembrane fluxes obtained in single-component experiments give a calculated separation factor of 6. However, when the feed solution contains 0.5M of each solute, the measured separation factor is 23. Data is presented in Table II. This illustrates again that $Ag^+$-Nafion® can be used to effectively separate compounds that have small and similar binding constants with $Ag^+$ in aqueous solutions.

Further, as the data in Table II demonstrates, compounds with similar aromatic structure but having differing non-aromatic portions (Cumene has a pendant isopropyl group while benzene has only pendent hydrogen moieties) can be readily separated using the subject ionopore membranes. This is evidence of a size/shape selective separation process.

TABLE II

THE FLUXES AND SEPARATION FACTORS OF BENZENE AND CUMENE THROUGH $Ag^+$ FORM NAFION ® 111

| Feed Concentration (M) | | Flux (mol/cm² · sec × $10^{-9}$) | | Separation |
|---|---|---|---|---|
| Benzene | Cumene | Benzene | Cumene | Factor |
| 0.00 | 0.50 | — | 0.62 | 6.0 |
| 0.50 | 0.00 | 3.7 | — | |
| 0.10 | 0.50 | 0.70 | 0.14 | 25 |
| 0.50 | 0.50 | 4.8 | 0.21 | 23 |
| 1.0 | 0.50 | 5.2 | 0.11 | 24 |

$K_{Ben}$ = 2.4
$K_{Cum}$ = 2.8

EXAMPLE 4

Experiments were also conducted involving a series of diene/monoene pairs. Four pairs, ranging from $C_5$ to $C_{10}$, were evaluated.

TABLE III

THE FLUXES AND SEPARATION FACTORS OF DIENES VS. MONOENES THROUGH $Ag^+$ NAFION ®111

| Feed Concentration (M) | | Flux × $10^9$ (mol/cm² · sec) | | Separation Factor |
|---|---|---|---|---|
| 1,4-Pentadiene | 1-Pentene | 1,4-Pentadiene | 1-Pentene | |
| 0.00 | 0.50 | — | 12 | } 1.3 |
| 0.50 | 0.00 | 16 | — | |
| 0.50 | 0.50 | 22 | 2.9 | 6.8 |
| 1,5-Hexadiene | 1-Hexene | 1,4-Hexadiene | 1-Hexene | |
| 0.00 | 0.50 | — | 4.0 | } 4.3 |
| 0.50 | 0.50 | 17 | — | |
| 0.50 | 0.50 | 19 | 0.44 | 43 |
| 1,7-Octadiene | 1-Octene | 1,7-Octadiene | 1-Octene | |
| 0.00 | 0.50 | — | 1.2 | } 2.3 |
| 0.50 | 0.00 | 2.7 | — | |
| 0.50 | 0.50 | 2.6 | 0.039 | 67 |
| 1,9-Decadiene | 1-Decene | 1,9-Decadiene | 1-Decene | |
| 0.00 | 0.50 | — | 0.20 | } 3.3 |
| 0.50 | 0.00 | 0.65 | — | |
| 0.50 | 0.50 | 0.69 | 0.0084 | 82 |

As Table III shows, the diene dominates the corresponding monoene in every case. Also evident from the table is the fact that the separation factors increase with the length of the solute pairs. The actual separation factor for 1,4-pentadiene/ 1-pentene is 6.8, while the actual separation factor for 1,9-decadiene/1-decene is 82.

The above results demonstrate that large separation factors for facilitated transport membranes are obtainable under conditions of high feed concentrations and with very thin membranes. These unexpected results are clearly due to absorption and mobility properties of olefins and aromatics in solution cast PFSA membranes that have been $Ag^+$ exchanged, such as in Nafion® membranes.

Having described the invention, the following is claimed:

1. A method for effectively separating an unsaturated hydrocarbon from a liquid hydrocarbon feedstock containing at least two unsaturated hydrocarbons which vary in molecular size and save substantially the same equilibrium constants comprising passing said feedstock over one side of an ionopore membrane having incorporated therein a facilitater, which has an affinity for each of said at least two unsaturated hydrocarbons, and recovering from a second side of said membrane a permeate containing predominantly an unsaturated hydrocarbon having a smaller molecular size than the remaining unsaturated hydrocarbons, wherein said unsaturated hydrocarbons are selected from the group consisting essentially of aromatic, alkene, and diene hydrocarbons.

2. The method of claim 1 wherein said facilitator is $Ag^+$.

3. The method of claim 1 wherein said ionopore membrane is a perfluorosulfonic acid (PFSA) membrane.

4. The method of claim 1 wherein said ionopore membrane is a solution-cast perfluorosulfonic acid (PFSA) membrane.

5. The method of claim 1 wherein said unsaturated hydrocarbons are hexadiene and hexene.

6. The method of claim 1 wherein said unsaturated hydrocarbons are styrene and ethylbenzene.

7. The method of claim 1 wherein said unsaturated hydrocarbons are $C_4$–$C_{12}$ diene/monoene pairs.

8. The method of claim 1 wherein said unsaturated hydrocarbons are cumene and benzene.

9. The method of claim 1 wherein said unsaturated hydrocarbons are benzene and alkyl-substituted benzenes selected from the group consisting essentially of toluene, xylene, and cumene.

10. A method for achieving liquid phase separation of at least two competing components which vary in molecular size from a feedstock containing said competing components comprising passing said feedstock over a facilitated perfluorosulfonic acid ionopore membrane and separating at least one said component having a smaller molecular size than the remaining components from the remaining components, the separation factor for the competing components as a mixture being at least about 4 times the separation factor measured for permeation of said one component or said remaining components alone using the same membrane and under the same operating conditions.

11. The method of claim 10 wherein said facilitated ionopore membrane contains $Ag^+$ facilitator.

12. The method of claim 10 wherein said ionopore membrane is a solution-cast perfluorosulfonic acid membrane.

13. The method of claim 10 wherein said competing components are hexadiene and hexene.

14. The method of claim 10 wherein said competing components are styrene and ethylbenzene.

15. The method of claim 10 wherein said competing components are $C_4$–$C_{12}$ diene/monoene pairs.

16. The method of claim 10 wherein said competing components are cumene and benzene.

17. The method of claim 10 wherein said competing components are benzene and alkyl-substituted benzenes selected from the group consisting essentially of toluene, xylene, and cumene.

18. A method for achieving liquid phase separation of at least two competing components from a feedstock containing said components wherein said separation is conducted through an ionopore membrane, exchanged with a complexing agent for which all competing components demonstrate substantially the same affinities, and one competing component having a smaller molecular size than the remaining competing components permeates said membrane more selectively than said remaining components.

19. A method for effectively separating an unsaturated hydrocarbon from a liquid hydrocarbon feedstock containing at least two unsaturated hydrocarbons which vary in molecular size and have substantially the same equilibrium constants comprising passing said feedstock over one side of an ionopore membrane having incorporated therein a facilitator, which has an affinity for each of said at least two unsaturated hydrocarbons, and recovering from a second side of said membrane a permeate containing predominantly one unsaturated hydrocarbon having a smaller molecular size than the remaining unsaturated hydrocarbons, wherein said unsaturated hydrocarbons are selected from the group consisting essentially of hexadiene/hexene, styrene/ethylbenzene, $C_4$–$C_{12}$ diene/monoene pain, cumene/benzene, benzene/toluene, and benzene/xylene.

20. A method for achieving liquid phase separation of at least two competing components from a feedstock containing said components comprising passing said feedstock over a facilitated ionopore membrane and separating one said component from a second said component, the separation factor for the competing components as a mixture being at least about 4 times the separation factor measured for permeation of said one component or said second component alone using the same membrane and under the same operating conditions, said competing components being selected from the group consisting essentially of hexadiene/hexene, styrene/ethylbenzene, $C_4$–$C_{12}$ diene/monene pairs, cumene/benzene, benzene/toluene, and benzene/xylene.

* * * * *